United States Patent [19]

Skobel

[11] 4,147,443
[45] Apr. 3, 1979

[54] HANDLE FOR A MEDICAL INSTRUMENT

[75] Inventor: Barry A. Skobel, Edison, N.J.

[73] Assignee: S & S Medical Products Co., Inc., Iselin, N.J.

[21] Appl. No.: 593,057

[22] Filed: Jul. 3, 1975

[51] Int. Cl.² .............................................. B25G 3/34
[52] U.S. Cl. ......................................... 403/267; 30/343
[58] Field of Search ..................... 403/265, 267, 269; 264/273; 401/6; 30/343; 145/61 A, 61 B, 61 C, 61 D

[56] References Cited

U.S. PATENT DOCUMENTS

| 972,305 | 10/1910 | Whittemore | 145/61 A UX |
| 2,205,769 | 6/1940 | Sweetland | 145/61 C |
| 2,382,304 | 8/1945 | Foltz et al. | 30/343 |
| 2,520,355 | 8/1950 | Bell | 30/343 |

Primary Examiner—Wayne L. Shedd
Attorney, Agent, or Firm—Friedman, Goodman & Teitelbaum

[57] ABSTRACT

A handle for a medical instrument having a handle portion. The handle portion is fabricated from metal, preferably stainless steel, and is provided with at least one annular channel disposed completely around the handle portion. An elastomer material, preferably silicone rubber, is molded on the handle portion to completely cover the handle portion, where the elastomer material extends into and fills the channel. The elastomer material provides pressure within the channel when the medical instrument is heated during steam sterilization thereof so that the elastomer material defines a seal within the channel to prevent moisture from passing between the covered handle portion and the elastomer material. Additionally, the handle portion may be provided with holes extending therethrough which are filled with the elastomer material to additionally secure the elastomer material to the handle portion.

10 Claims, 12 Drawing Figures

HANDLE FOR A MEDICAL INSTRUMENT

BACKGROUND OF THE INVENTION

The present invention relates generally to a handle, and more particularly to a handle for a medical instrument where an elastomer material is molded onto the handle portion to cover same.

Medical instruments or tools are usually formed from metal, preferably stainless steel, and are required to be steam sterilized after each use thereof. Many attempts have been made to provide these medical instruments with non-metal handles to facilitate the use thereof. However, the handles known in the prior art have not been satisfactory, where they have not been able to withstand the steam sterilization process. Some of the difficulties encountered are that the steam sterilization has caused the non-metal handle to crack, or during the sterilization thereof, moisture has gotten between the metal handle portion and the non-metal handle causing the handle to separate from the handle portion so that the handle comes off or is dislodged from the handle portion during use thereof.

Metal handles have also been used on the handle portion of the medical instrument, but these metal handles add substantial weight to the handle end of the instrument. Accordingly, this additional weight causes the instrument to be unbalanced and therefore is not easily used by the surgeon or physician. Furthermore, this additional weight causes the physician to become fatigued, particularly when using the instrument for a long period of time.

SUMMARY OF THE INVENTION

Accordingly, it is an object of the present invention to provide a handle for a medical instrument which overcomes the disadvantages of the prior art.

It is another object of the present invention to provide a handle for a medical instrument that can be repeatedly steam sterilized without separation from the handle portion of the medical instrument.

It is a further object of the present invention to provide a handle for a medical instrument that is of light weight, one that permits a firm grasp of the medical instrument and which provides strength, stability, balance and a tactile sensitivity during the use of the instrument.

It is a still further object of the present invention to provide a handle for a medical instrument having an elastomer material molded on a metal handle portion where the elastomer material does not separate from the metal handle portion during steam sterilization thereof.

It is an added object of the present invention to provide a handle as mentioned above having at least one annular channel disposed completely around the handle portion, the channel being completely filled with the elastomer material to prevent moisture from passing between the covered handle portion and the elastomer material.

And yet another added object of the present invention is to provide a handle as mentioned above wherein the elastomer material has a coefficient of expansion greater than the coefficient of expansion of the metal handle portion so that the elastomer material provides pressure within the channel to define a seal therein.

And yet another object of the present invention is to provide a handle as mentioned above provided with holes extending through the handle portion to receive the elastomer material therein for securement between the elastomer material and the handle portion.

To this end, the present invention relates to a handle for a medical instrument comprising a handle portion fabricated from metal and covered with an elastomer material which is molded thereon, the elastomer material filling at least one annular channel provided on and completely disposed around the handle portion, the elastomer material having a coefficient of expansion greater than the coefficient of expansion of the metal handle portion to have the elastomer material provide pressure within the channel when the medical instrument is heated during steam sterilization thereof so that the elastomer material defines a seal within the channel to prevent moisture from passing between the covered handle portion and the elastomer material. The handle portion can be fabricated in any desired shape, such as having a circular or rectangular cross section. Preferably, holes are provided through the handle portion to receive the elastomer material therein for securement of the elastomer material to the covered handle portion. Preferbly, the elastomer material is silicone rubber, and the handle portion is fabricated from stainless steel. The handle may be either positioned at one end of the medical instrument or along the length thereof.

BRIEF DESCRIPTION OF THE DRAWINGS

With the above and additional objects and advantages in view, as will hereinafter appear, this invention comprises the devices, combinations and arrangements of parts hereinafter described by way of example and illustrated in the accompanying drawings of a preferred embodiment in which.

DETAILED DESCRIPTION OF THE PREFERRED EMBODIMENTS

Figure 1:
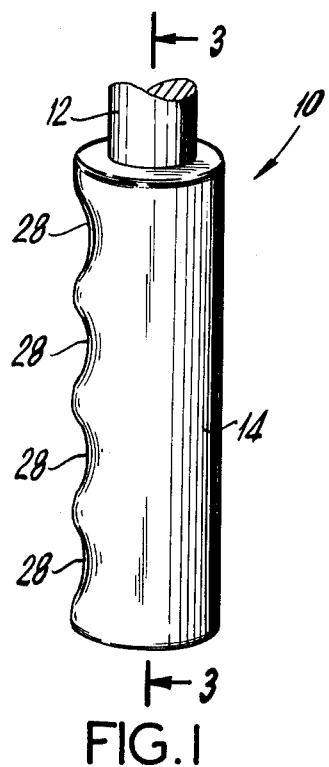
FIG. 1 illustrates a fragmentary perspective view of a handle for a medical instrument according to the present invention.

Referring now to the drawings, and more specifically to FIG. 1, the present invention comprises a handle for a medical instrument generally denoted by the reference character 10. The remaining portion of the medical instrument does not form a part of the present invention, and therefore, is not shown, where the remaining portion may have any desired configuration well known in the art. The handle 10 includes a handle portion 12 which is integrally formed as a one-piece unit with the remaining portion of the medical instrument, and a cover or grip member 14 which is disposed over the handle portion 12, as will be discussed hereinafter below.

Figure 2:
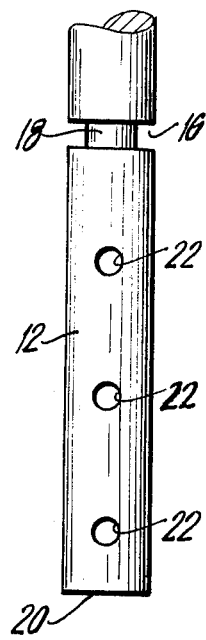
FIG. 2 illustrates a fragmentary elevational view of the handle portion before the elastomer material is molded thereon.

The handle portion 12, and therefore the remaining portion of the medical instrument, is fabricated from metal, preferably 316L stainless steel, or Vanadium, Titanium and like metals. The handle portion 12 is circular or round about the longitudinal axis as indicated in FIG. 2 showing the uncovered handle portion 12. A groove 16 is provided in the handle portion 12, being radially disposed around the longitudinal axis of the handle portion 12 to define an annular channel disposed completely around the handle portion 12. The floor of the groove or channel 16 is denoted by the reference character 18. The groove 16 is sufficiently longitudinally spaced from the free end 20 of the handle portion 12 to permit the surgeon to have a firm grasp of the instrument between the groove 16 and the end 20. Additionally, a plurality of apertures, openings or holes 22 extend completely through the handle portion 12, in a spaced apart arrangement, the function of which will be discussed hereinafter below.

Figure 3:
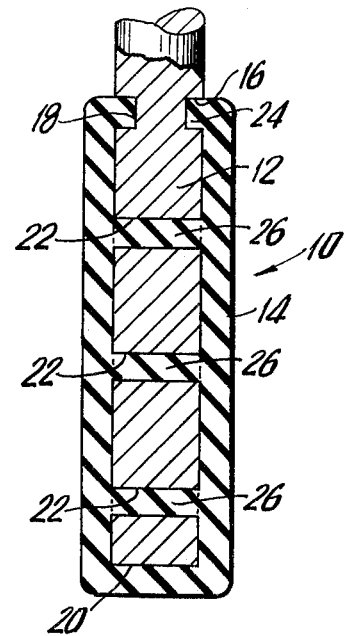
FIG. 3 illustrates a fragmentary cross sectional view taken along the line 3—3 in FIG. 1.

The grip member 14 is fabricated from an elastomer material, preferably silicone rubber. The elastomer material is molded on the handle portion 12 to completely cover the handle portion from the groove 16 to the end 20, where the elastomer material encloses the end 20 as best shown in FIG. 3. The elastomer material also extends into and fills the groove 16 to define a seal 24 which abuts against the floor 18 and sidewalls of the groove 16. Additionally, portions 26 of the elastomer material fill the holes 22 to provide additional securement between the grip member 14 and the handle portion 12, where the elastomer material portions 26 are locked within the holes 22 and thereby prevent longitudinal movement of the grip member 14 relative to the handle portion 12.

The silicone rubber has a coefficient of linear expansion of 0.000485, and the 316L stainless steel has a coefficient of linear expansion of 0.0000049, thus the silicone rubber expands approximately 100 times more than the stainless steel. Accordingly, when the medical instrument is heated during the steam sterilization thereof, the silicone rubber seal 24 expands approximately 100 times the amount of the stainless steel sidewalls of the groove 16, so that the seal 24 exerts a great amount of pressure against the sidewalls of the groove 16 during sterilization thereof. Accordingly, this pressure of the elastomer material within the groove 16 prevents any moisture from passing into the groove 16 and between the covered handle portion 12 and the grip member 14. As stated above, such moisture would cause the grip member 14 to separate from the handle portion 12 so that the grip member 14 in time, after repeated sterilization thereof, would come off or be dislodged from the handle portion 12 during the use thereof. Thus, the silicone rubber seal 24 prevents the dislodgement of the grip member 14.

It is further noted, that the density of silicone rubber is approximately 0.042 pounds per cubic inch, where the density of 316L stainless steel is approximately 0.29 pounds per cubic inch, so that the stainless steel is approximately seven times heavier than the silicone rubber. Thus, the silicone rubber grip member 14 is of a light weight, which allows the medical instrument to be easily balanced and used by the surgeon. Furthermore, this light weight enables the surgeon to use the medical instrument for long periods of time without becoming fatigued. Additionally, the grip member 14 is provided with finger grooves 28, to define a fist grip which permits a firm grasp of the instrument which provide strength, stability, balance and a tactile sensitivity during the use of the medical instrument.

Figure 4:
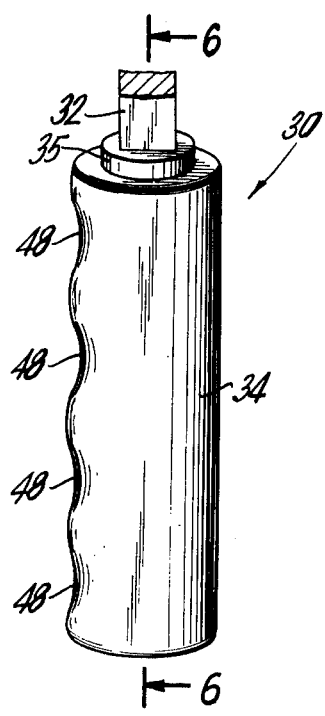
FIG. 4 illustrates a fragmentary perspective view of a modified handle for a medical instrument according to the present invention.
Figure 5:
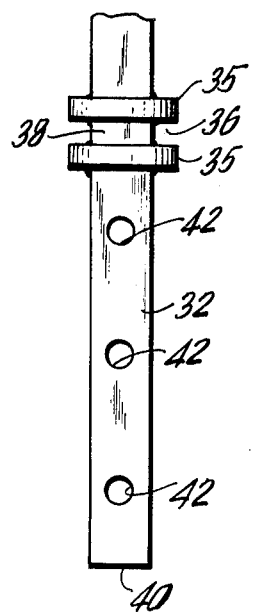
FIG. 5 illustrates a fragmentary elevational view of the handle portion of FIG. 4 before the elastomer material is molded thereon.
Figure 6:
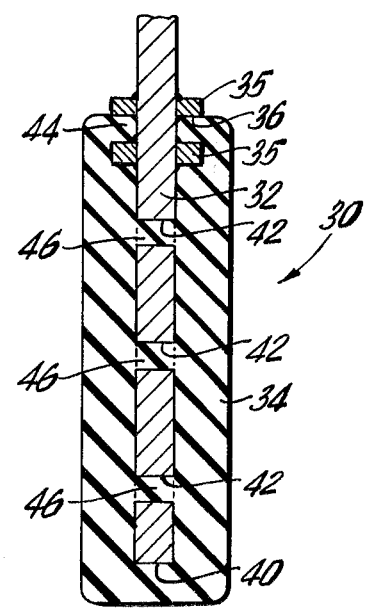
FIG. 6 illustrates a fragmentary cross sectional view taken along the line 6—6 in FIG. 4.

A modified handle 30 for a medical instrument according to the present invention is shown in FIGS. 4, 5 and 6. In this embodiment, the handle portion 32 has four planar surfaces to provide a rectangular cross section as best indicated in FIG. 6. As mentioned above, the handle portion 32 is fabricated from metal, preferably 316L stainless steel. Furthermore, as shown in FIG. 4, a cover or grip member 34 is disposed over the handle portion 32 in a similar manner as mentioned above, as will be discussed hereinafter below.

As shown in the uncovered handle portion 32 in FIG. 5, a pair of ring-like members 35 are secured on the handle portion 32 in a spaced apart relationship to define an annular channel 36 disposed completely around the handle portion 32. The ring-like members 35 are also preferably fabricated from 316L stainless steel and have openings therein to receive the handle portion 32. The ring-like members 35 are secured to the handle portion 32 by conventional securing means such as by welding, solder and the like which also function to close any unfilled portions of the openings in the ring-like members 35. The floor of the channel 36 is denoted by the reference character 38.

The groove 36 is sufficiently longitudinally spaced from the free end 40 of the handle portion 32 to permit the surgeon to have a firm grip of the instrument between the groove 36 and the end 40. Additionally, a plurality of apertures, openings or holes 42 extend completely through the handle portion 32, in a spaced apart arrangement, to function in a similar manner as the above-mentioned holes 22 in the handle portion 12.

The grip member 34, like the grip member 14, is fabricated from an elastomer material, preferably silicone rubber. In a similar manner as mentioned above, the elastomer material is molded on the handle portion 32 to completely cover the handle portion from the channel 36 to the end 40, where the elastomer material encloses the end 40 as best shown in FIG. 6. The elastomer material extends into and fills the channel 36 to define a seal 44 which abuts against the floor 38 and the sidewalls of the ring-like members 35 forming the channel 36. Portions 46 of the elastomer material fill the hole 42 to provide additional securement between the grip member 34 and the handle portion 32, in the same manner as mentioned above to prevent longitudinal movement of the grip member 34 relative to the handle portion 32.

The silicone rubber of the grip member 34 and the stainless steel of the handle portion 32 react in a similar manner as mentioned above, so that the seal 44 exerts a great amount of pressure against the sidewalls of the ring-like members 35 defining the groove 36 during the steam sterilization thereof. Accordingly, this pressure of the elastomer material within the channel 36 prevents any moisture from passing into the channel 36 and between the covered handle portion 32 and the grip member 34. Thus, the silicone rubber seal 44 prevents the dislodgement of the grip member 34 which is usually caused by moisture separating the parts.

Additionally, the silicone rubber grip member 34 is of a light weight, which allows the medical instrument to be easily balanced and used by the surgeon. Furthermore, the grip member 34 is provided with finger grooves 48, to define a fist grip as mentioned above.

Figure 7:
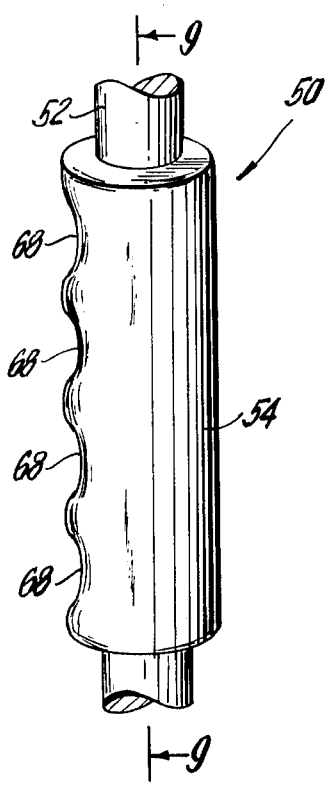
FIG. 7 illustrates a fragmentary perspective view of a second modified handle for a medical instrument according to the present invention.
Figure 8:
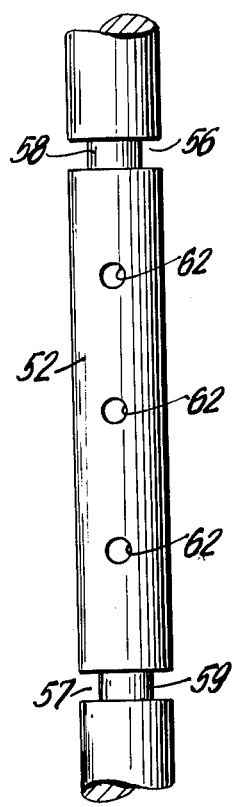
FIG. 8 illustrates a fragmentary elevational view of the handle portion of FIG. 7 before the elastomer material is molded thereon.
Figure 9:
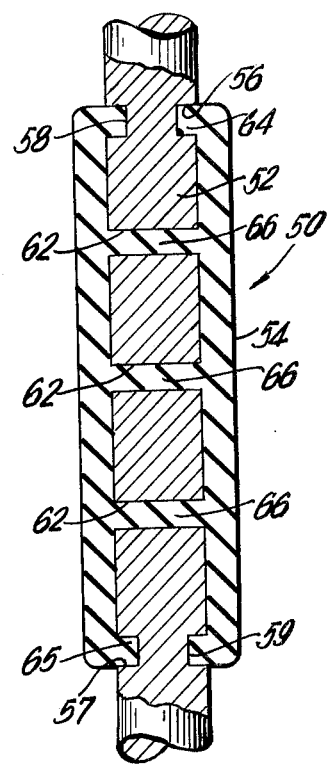
FIG. 9 illustrates a fragmentary cross sectional view taken along the line 9—9 in FIG. 7.

A second modified handle 50 for a medical instrument according to the present invention is shown in FIGS. 7, 8 and 9. In this embodiment, the handle portion 52 is circular or round about the longitudinal axis, as indicated in FIG. 8 showing the uncovered handle portion 52. The handle 50 is spaced from the end of the medical instrument, being disposed along the length thereof, such as being centrally located on the medical instrument, so that the medical instrument may have a tool at both ends thereof. As mentioned above, the handle portion 52 is fabricated from metal, preferably 316L stainless steel. Furthermore, as shown in FIG. 7, a cover or grip member 54 is disposed over the handle portion 52, as will be discussed hereinafter below.

A pair of grooves 56, 57 is provided in the handle portion 52, being spaced apart and radially disposed around the longitudinal axis of the handle portion 52 to define annular channels disposed completely around the handle portion 52. The floor of each groove or channel 56, 57 is denoted by the reference characters 58, 59 respectively. The grooves 56, 57 are sufficiently longitudinally spaced apart from each other to permit the surgeon to have a firm grasp of the instrument therebetween when the grip member 54 is disposed thereon. Additionally, a plurality of apertures, openings or holes 62 extend completely through the handle portion 52, in a spaced apart arrangement, to function in a similar manner as mentioned above.

The grip member 54, like the above-mentioned grip members, is fabricated from an elastomer material, preferably silicone rubber. In a similar manner as mentioned above, the elastomer material is molded on the handle portion 52 to completely cover the handle portion from the channel 56 to the channel 57, as best shown in FIG. 9, where the elastomer material extends into and fills each channel 56, 57 to define seals 64, 65 at opposite ends of the grip member 54. The seals 64, 65 abut against the floors 58, 59 and the sidewalls of the associated grooves 56, 57. Furthermore, the portions 66 of the elastomer material fill the holes 62 to provide additional securement between the grip member 54 and the handle portion 52, in the same manner as mentioned above, to prevent longitudinal movement of the grip member 54 relative to the handle portion 52.

The silicone rubber of the grip portion 54 and the stainless steel of the handle portion 52 react in a similar manner as mentioned above, so that the seals 64, 65 exert a great amount of pressure against the sidewalls of the associated grooves 56, 57 during the steam sterilization thereof. Accordingly, this pressure of the elastomer material within the channels 56, 57 prevents any moisture from passing into the channels 56, 57 and between the covered handle portion 52 and the grip member 54. Thus, the silicone rubber seals 64, 65 prevent the dislodgement of the grip member 54 which is usually caused by moisture separating the part.

Additionally, as mentioned above, the silicone rubber grip member 54 is of a light weight, which allows the medical instrument to be easily balanced and used by the surgeon. Furthermore, the grip member 54 is provided with finger grooves 68, to define a fist grip as mentioned above.

Figure 10:
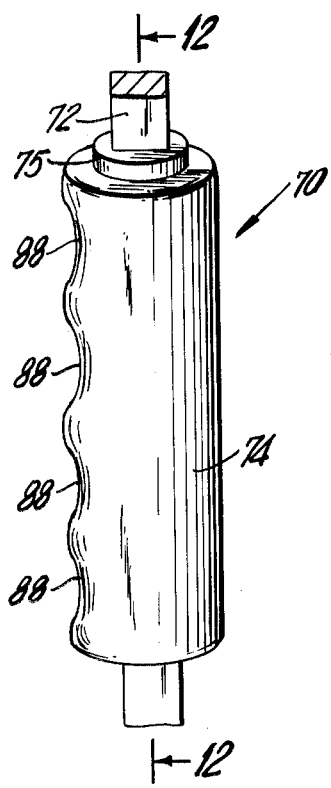
FIG. 10 illustrates a fragmentary perspective view of a third modified handle for a medical instrument according to the present invention.
Figure 11:
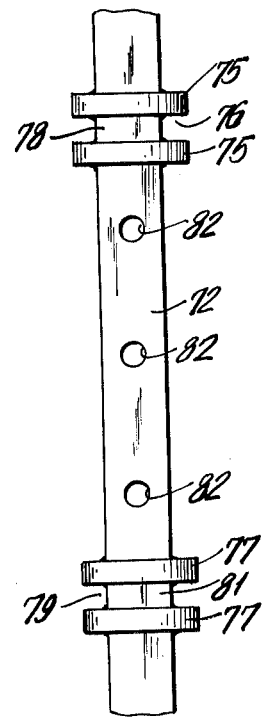
FIG. 11 illustrates a fragmentary perspective view of the handle portion of FIG. 10 before the elastomer material is molded thereon.
Figure 12:
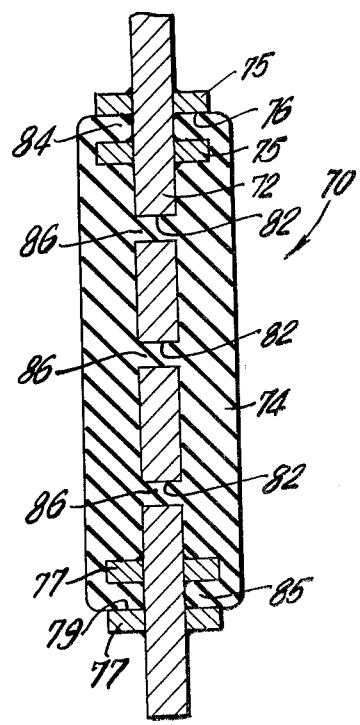
FIG. 12 illustrates a fragmentary cross sectional view taken along the line 12—12 in FIG. 10.

A third modified handle 70 for a medical instrument according to the present invention is shown in FIGS. 10, 11 and 12. In this embodiment, the handle portion 72 is also spaced from the end of the medical instrument, being disposed along the length thereof, such as being centrally located on the medical instrument, so that the medical instrument may have a tool at both ends thereof. The handle portion 72 has four planar surfaces to provide a rectangular cross section as best shown in FIG. 12. As mentioned above, the handle portion 72 is fabricated from metal, preferably 316L stainless steel. Furthermore as shown in FIG. 10, a cover or grip member 74 is disposed over the handle portion 72 in a manner as mentioned above, as will be discussed hereinafter below.

As shown in the uncovered handle portion 72 in FIG. 11, two pairs of ring-like members 75, 77 are secured on the handle portion 72, each pair being spaced apart to define an annular channel 76, 79 disposed completely around the handle portion 72. The ring-like members 75, 77 are also preferably fabricated from 316L stainless steel and have openings therein to receive the handle portion 72. The ring-like members 75, 77 are secured to the handle portion 72 by conventional securing means, such as by welding, solder and the like, which also functions to close any unfilled portions of the openings in the ring-like members 75, 77. The floor of the channels 76, 79 are denoted by the reference characters 78, 81, respectively.

The groove 76 is sufficiently longitudinally spaced from the other groove 79 to permit the surgeon to have a firm grip of the instrument between the grooves 76, 79 when the grip member 74 is disposed thereon. Additionally, a plurality of apertures, openings or holes 82 extend completely through the handle portion 72, in a spaced apart arrangement, to function in a similar manner as mentioned above.

The grip member 74, like the above-mentioned grip members, is fabricated from an elastomer material, preferably silicone rubber. In a similar manner as mentioned above, the elastomer material is molded on the handle portion 72 to completely cover the handle portion from the channel 76 to the channel 79, as best shown in FIG. 12, where the elastomer material extends into and fills each channel 76, 79 to define seals 84, 85 at opposite ends of the grip member 74. The seals 84, 85 abut against the floors 78, 81 and the sidewalls of the ring-like members 75, 77 forming the channels 76, 79. Furthermore, the portions 86 of the elastomer material fill the holes 82 to provide additional securement between the grip member 74 and the handle portion 72, in the same manner as mentioned above, to prevent longitudinal movement of the grip member 74 relative to the handle portion 72.

Here again, the silicone rubber of the grip portion 74 and the stainless steel of the handle portion 72 react in a similar manner as mentioned above, so that the seals 84, 85 exert a great amount of pressure against the sidewalls of the ring-like members 75, 77 defining the grooves 76, 79 during the steam sterilization thereof. Accordingly, this pressure of the elastomer material within the channels 76, 79 prevents any moisture from passing into the channels 76, 79 and between the covered handle portion 72 and the grip member 74. Thus, the silicone rubber seals 84, 85 prevents the dislodgement of the grip member 74 which is usually caused by moisture separating the parts.

Additionally, as mentioned above, the silicone rubber grip member 74 is of a light weight which allows the medical instrument to be easily balanced and used by the surgeon. Furthermore, the grip member 74 is provided with finger grooves 88, to define a fist grip as mentioned above.

It is further noted, that if additional securement between any of the grip members and their associated handle portions is desired, an adhesive or bonding agent may be disposed therebetween, such securing means being well known in the art.

Numerous alterations of the structure herein disclosed will suggest themselves to those skilled in the art. However, it is to be understood that the present disclosure relates to a preferred embodiment of the invention which is for purposes of illustration only and is not to be construed as a limitation of the invention.

What is claimed is:

1. A handle for a medical instrument comprising a handle portion of the medical instrument, said handle portion being fabricated from metal, said handle portion including at least one annular channel spaced from an end of the medical instrument, said channel being disposed completely around said handle portion, elastomer sealing means having a coefficient of expansion greater than coefficient of expansion of said metal handle portion, said elastomer sealing means being disposed against sidewalls of said channel and filling said channel, a major portion of said elastomer sealing means extending from said channel and being disposed against said metal handle portion for covering said metal handle portion, said elastomer sealing means providing pressure within said channel and preventing moisture from passing through said channel and from penetrating between said metal handle portion and said elastomer sealing means when the medical instrument is heated during steam sterilization thereof.

2. A handle as claimed in claim 1, wherein said elastomer means is silicone rubber.

3. A handle as claimed in claim 1, wherein said handle portion is provided with holes extending therethrough in a spaced apart arrangement, said elastomer means filling said holes to increase securement between said elastomer means and said handle portion.

4. A handle as claimed in claim 1, wherein said elastomer means is provided with finger grooves on an outer surface to define a fist grip to permit a firm grasp of the medical instrument.

5. A handle as claimed in claim 1, wherein said handle portion is circular about its longitudinal axis, said annular channel being a groove radially disposed around the longitudinal axis of said circular handle portion.

6. A handle as claimed in claim 5, wherein said handle portion is provided with holes extending therethrough in a spaced apart arrangement, said elastomer means filling said holes to increase securement between said elastomer means and said handle portion, said elastomer means being provided with finger grooves on an outer surface to define a fist grip to permit a firm grasp of the medical instrument, said elastomer means being silicone rubber.

7. A handle as claimed in claim 1, wherein said handle portion has four planar surfaces to define a rectangular cross section, a pair of ring-like members being secured on said handle portion in a spaced apart relationship to provide said annular channel.

8. A handle as claimed in claim 7, wherein said handle portion is provided with holes extending therethrough in a spaced apart arrangement, said elastomer means filling said holes to increase securement between said elastomer means and said handle portion, said elastomer means being provided with finger grooves on an outer surface to define a fist grip to permit a firm grasp of the medical instrument, said elastomer means being silicone rubber.

9. A handle as claimed in claim 1, wherein said end of the medical instrument is a part of said handle portion, said elastomer means enclosing said end and extending from said end to said channel to provide a hand grip member.

10. A handle as claimed in claim 1, wherein said handle portion includes a second annular channel spaced apart from said first memtioned annular channel, both of said annular channels being filled with said elastomer means to define seals at opposite ends of said elastomer means, said elastomer means extending from one of said channels to the other of said channels to provide a hand grip member.

* * * * *